United States Patent [19]

Wilkins

[11] Patent Number: 4,986,271
[45] Date of Patent: Jan. 22, 1991

[54] VIVO REFILLABLE GLUCOSE SENSOR

[75] Inventor: Ebtisam S. Wilkins, Albuquerque, N. Mex.

[73] Assignee: The University of New Mexico, Albuquerque, N. Mex.

[21] Appl. No.: 382,603

[22] Filed: Jul. 19, 1989

[51] Int. Cl.$^5$ ............................................. A61B 5/00
[52] U.S. Cl. .................................. 128/635; 204/403; 204/415; 435/817
[58] Field of Search ............... 128/635; 204/403, 415; 435/817; 436/806

[56] References Cited

U.S. PATENT DOCUMENTS

| | | | |
|---|---|---|---|
| 3,979,274 | 9/1976 | Newman | 204/195 B |
| 4,224,125 | 9/1980 | Nakamura et al. | 204/195 B |
| 4,240,438 | 12/1980 | Updike et al. | 128/635 |
| 4,376,689 | 3/1983 | Nakamura et al. | 204/195 B |
| 4,418,148 | 11/1983 | Oberhardt | 435/179 |
| 4,655,880 | 4/1987 | Liu | 204/1 T |
| 4,703,756 | 11/1987 | Gough et al. | 123/635 |
| 4,795,542 | 1/1989 | Ross et al. | 204/415 |
| 4,805,624 | 2/1989 | Vao et al. | 128/635 |
| 4,830,713 | 5/1989 | Gagescu | 204/415 |

FOREIGN PATENT DOCUMENTS 0257302 6/1988 Fed. Rep. of Germany ...... 204/403
0446820 10/1974 U.S.S.R. .............................. 204/415

Primary Examiner—Lee S. Cohen
Assistant Examiner—K. M. Pfaffle
Attorney, Agent, or Firm—Albert Sopp

[57] ABSTRACT

An arrangement for prolonging the useful life of an electrochemical refillable implantable glucose sensor employing an enzyme material such as glucose oxidase immobilized on bulk particulate matter suspended in a fluid for reaction with components of bodily fluids and which enzyme material when exhausted or degraded after reaction may be replaced by fresh enzyme-loaded particles.

9 Claims, 3 Drawing Sheets

VIVO REFILLABLE GLUCOSE SENSOR

FIELD OF INVENTION

This invention relates to a refillable implantable glucose sensor employing an enzyme such as glucose oxidase immobilized on a bulk powder such as very fine graphite particles which can be exhausted from the implanted sensor when spent and replaced by fresh enzyme-loaded particles, thereby prolonging the useful life of the implanted sensor.

BACKGROUND OF THE INVENTION

Glucose sensors of the type employing enzymes are well known. Many of these feature an "enzyme electrode" which consists of an immobilized enzyme such as glucose oxidase that catalyzes a chemical reaction involving glucose and oxygen—a reaction that involves the catalytic conversion of glucose to gluconic acid with simultaneous consumption of oxygen. The resulting decrease in oxygen may be measured by a current sensitive oxygen electrode.

Various arrangements for glucose sensors are described in the following U.S. Pats: U.S. Pat. No. 4,703,756 which utilizes first and second tandem sensor elements mounted in a catheter, one of which sensors acts as a reference and the other of which contacts glucose oxidase, whereby an electrical signal is produced indicative of the oxygen content differential between the two sensors; U.S. Pat. No. 4,240,438 which uses a hydrophobic membrane on which the glucose oxidase is immobilized and which senses the rate of oxygen consumption by the glucose contained in the blood; U.S. Pat. No. 4,655,880 which provides a multiple electrode sensor for measurement of glucose concentration by comparing electron current flow in working and counter electrodes in relation to current flow in a reference electrode; U.S. Pat. No. 3,979,274 which utilizes a laminated enzyme electrode with special filtering properties thereby eliminating the need for a compensating or reference electrode; U.S. Pat. No. 4,224,125 which has an enzyme electrode using an oxidoreductase and a redox copolymer acting as an electron mediator in an enzymatic reaction maintained in an immobilized state on an electron collector or semipermeable membrane; U.S. Pat. No. 4,376,689 wherein the coenzyme is immobilized directly on an electron collector [eliminating the need for a membrane] whereby the activity of the enzyme on a substrate can be directly measured; U.S. Pat. No. 4,418,148 employing a contiguous multilayer membrane structure enabling a more homogeneous distribution of enzyme.

At present there does not exist an enzyme type glucose sensor providing the advantage especially for use in vivo [i.e., implantable] whereby the spent enzyme material may be replaced transcutaneously.

SUMMARY OF THE INVENTION

The present invention provides an improved arrangement for an implantable electrochemical sensor such as a glucose sensor of the type in which the enzyme material degrades due to reaction with components of bodily fluids, the improvement being that the degraded enzyme material can be periodically replaced with fresh enzyme material while the sensor remains implanted, thus prolonging the useful implanted life of the sensor.

According to one embodiment of the present invention there is provided a bulk powder of fine particles each carrying immobilized enzyme material. The bulk powder is carried as a suspension in a fluid such as a saline water solution and thus may be transcutaneously injected into and discharged from an implanted sensor. The sensor has a housing defining an outer chamber bounded at its working end by an outer, hydrophilic membrane which enables bodily fluids to interact with a cathode and a reference electrode situated in the outer chamber. Within the outer chamber is an inner chamber bounded by an inner, hydrophobic membrane and containing a platinum anode adjacent the inner membrane. The inner membrane passes molecules such as glucose but not large molecules, water, or bodily fluids. The inner chamber contains enzyme material such as glucose oxidase material immobilized on particles of the bulk powder. The glucose oxidase reacts with the incoming glucose to deplete oxygen, and this is sensed by the anode to detect the amount of glucose.

Also, in accordance with another embodiment of the invention, the stability of the enzyme material may be further improved by providing in the sensor an additional or central chamber containing a replenishable catalase enzyme material immobilized on particles of bulk powder carried in a suspension. The catalase material removes and neutralizes the hydrogen peroxide produced by the reaction of glucose with glucose oxidase. The inner and central chambers each have recharge and discharge tubes fluidly coupled to respective implanted charge and discharge reservoirs. The tubes channel the bulk powder in suspension carrying the fresh and spent glucose oxidase and catalase enzyme materials. The anode, cathode, and reference electrode are each electrically or electromagnetically coupled transcutaneously to signal processing and monitoring circuitry positioned outside the body.

BRIEF DESCRIPTION OF THE DRAWINGS

Reference is now made to the accompanying drawings in which like numerals represent like parts and in which.

DETAILED DESCRIPTION OF THE INVENTION

Figure 1:
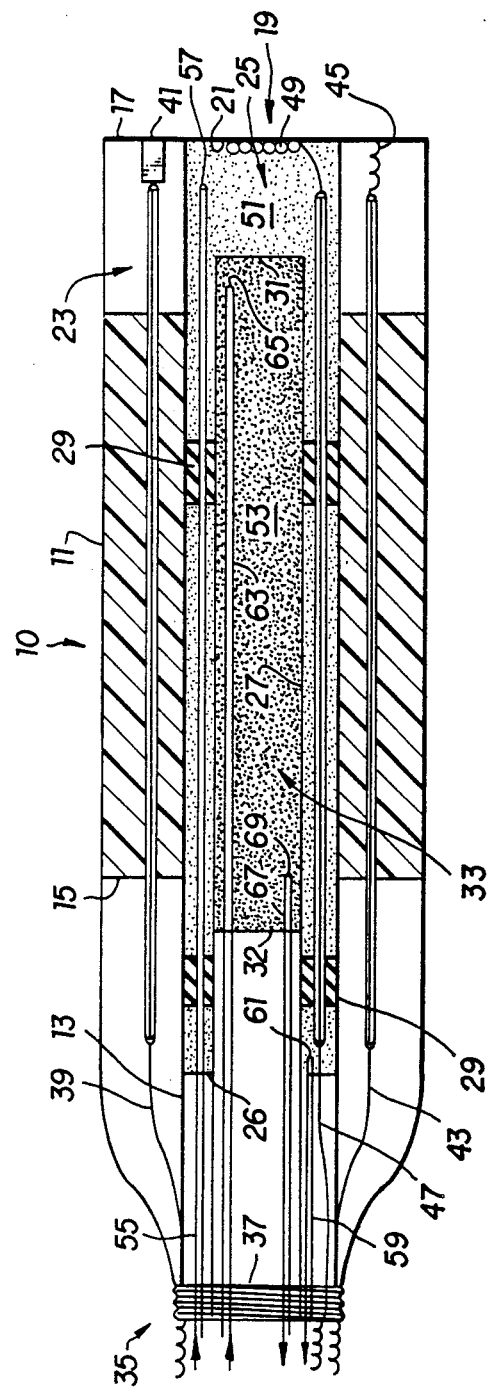
FIG. 1 is a cutaway view in longitudinal cross section of a glucose sensor in accordance with an emobodiment of the invention.

According to the embodiment of the invention shown in FIG. 1, a glucose sensor 10 in accordance with the principles of the invention has a generally cylindrical housing 11 of any suitable inert material which does not deleteriously react with bodily fluids or tissue. Located within the housing 11 is a generally cylindrical inner housing 13 of like inert material supported in spaced apart relation from the housing 11 by an annular member 15, also of inert material. An outer membrane 17 made of any suitable well-known hydrophilic material spans the extent of one end of the the housing 11, hereinafter referred to as the working end 19 of sensor 10.

An inner membrane 21 made of any suitable well-known hydrophobic material covers the working end of the inner housing 13. The inner membrane 21 underlies the outer membrane 17. Consequently, the spaced apart housings 11 and 13 together with their respective membranes 17 and 21 define an outer annular reaction chamber 23 and an inner reaction chamber 25 concentric therewith. The inner chamber 25 is effectively enclosed or bounded at its working end by both the membranes 17 and 21 and at its other end by a fluidtight transverse wall 26.

Also, according to an embodiment of the invention there may be provided a central housing 27 located within the inner housing 13 and held in spaced apart relation therefrom by annular spacers 29. The spacers 29 may be in the form of spoked rings of inert material so that enzyme material may easily pass longitudinally back and forth therethrough in the chamber 25. The central housing 27 has a hydrophobic membrane 31 at the sensor's working end 19 spaced apart from the membrane 21 and at its other end a transverse wall 32. The housing 27, wall 32, and membrane 31 define a central chamber 33.

The other end of the sensor 10, referred to hereinafter as the feed end 35 for purposes of convenience, has a fluid tight seal 37 made of any suitable well-known material non-reactive with bodily fluids. The seal 37 defines the closed other end of the outer annular reaction chamber 23 and can, if desired, be used in place of transverse walls 26 and 32 to define the closed end of the inner chamber 25 and the central chamber 33.

An insulated, electrically conducting lead 39 passes fluidtightly through the seal 37 and extends longitudinally through the spacer member 15 into chamber 23. A reference electrode 41 composed of both silver and silver chloride is electrically connected to the lead 39 in the chamber 23. The reference electrode 41 may be immediately adjacent to or in intimate physical contact with the outer membrane 17.

Another insulated electrically conducting lead 43 passes fluidtightly through the seal 37 and longitudinally through the spacer member 15 and terminates in the outer annular chamber 23 at a cathode or counter electrode 45 made of any suitable noble metal in the form of a helix or mesh or other suitable configuration to provide a large area of reaction located adjacent to or in intimate physical contact with the outer membrane 17. A third insulated electrical lead 47 passes through the seal 37 and terminates in the inner chamber 25 at a helical platinum anode or working electrode 49 immediately adjacent to or in intimate physical contact with the inner membrane 21.

The outer membrane 17 is of any suitable well-known material to permit the passage of bodily fluids therethrough into the chamber 23. Membrane 17 prevents the entry of large proteins or other large molecules or particulate matter into the chamber 23. The hydrophobic inner membrane 21 operates through molecular diffusion and is of any suitable well known material to enable the passage therethrough into the chamber 25 of only small molecules including limited amounts of glucose which may be present in bodily fluids. Water, large molecules, and large amounts of glucose are excluded by the membrane 21.

The inner chamber 25 is filled with the enzyme material such as glucose oxidase immobilized on and bonded to, i.e., fixed to, bulk powder material which is preferably electrically conductive and may comprise very fine particles of graphite, indicated by the numeral 51. Alternatively, the material 51 may be constituted of very fine particles of nylon, polyethylene, polystyrene, or electrically conducting polymers. The response or reaction time of the enzymes is advantageously somewhat shorter where the enzymes are carried on particles, especially electrically conductive particles, such as graphite. This reaction time is longer where the enzymes are fixed as in the prior art, on probes, rods, or membranes. This is due to the movement of the particles and the better contact because of the small size and the electrical conductivity of the particles. The central chamber is filled with a catalase enzyme material generally indicated by the numeral 53. The catalase enzyme material is also immobilized and bonded, i.e., fixed, to very fine particles of graphite in the same manner as the glucose oxidase.

The glucose oxidase enzyme material 51 for chamber 25 may be prepared as set forth in the following Example 1.

EXAMPLE 1.

[a] Add 10 mg of glucose oxidase to 42.5 Bovine Serum Albumin and 0.19 ml of 2.5% Gluteraldehyde to provide a cross-linked enzyme;

[b] To provide covalent linking of the glucose oxidase on modified graphite [i.e., glucose oxidase immobilized on the particles], [1] add 2 g of fine graphite powder about 44 microns in diameter or less particle size to 0.15 M 1-cyclohexl-3-(2)morpholinoethyl, carbodiimide, metho-p-toluene sulfonate in 5 ml of 0.1 M acetate buffer pH 4.5 at 20 degrees centigrade for 2 hours, [2] wash thoroughly with distilled water, then add 2 ml of 10 mg/ml glucose oxidase in 0.1 M acetate buffer pH 4.5 at 4 degrees C for 3 hours, and [3] wash with distilled water and dry in room temperature air; store the dry powder in refrigerator;

[c] Add 120 mg of the immobilized glucose oxidase produced as in [b] above to the cross linked enzyme produced in [a] above.

The catalase 53 for chamber 33 is produced as follows:

[d] Add 1.8 mg catalase to 42.5 mg Bovine Serum Albumin and 0.19 ml of 2.5% Gluteraldehyde;

[e] Add 120 mg of fine graphite powder with catalase immobilized thereon in the same manner as described in [b] above for glucose oxidase. [End of Example.]

Also extending fluidtightly through the seal 37 is an injection or charge tube 55 for introducing fresh enzyme material such as glucose oxidase into the inner chamber 25. The tube 55 terminates in an opening 57 located in the inner chamber 25 near the inner membrane 21. A discharge or exhaust tube 59 for expelling spent enzyme material from the chamber 25 has its opening 61 located near the feed end 35 of the sensor.

A catalase enzyme charge tube 63 passes fluidtightly through the seal 37 into the central chamber 33 and has its open end 65 near the membrane 31. A catalase discharge or exhaust tube 67 also passes fluidtightly through the seal 37 into the central chamber 33 and has its open end 69 near the feed end 35 of the sensor and thus, its open end is relatively remote from the membrane 31. As is well known in the art, the catalase enzyme serves to decompose hydrogen peroxide generated by the oxidation of the glucose occurring in the inner chamber 25. This prolongs the useful life of the glucose oxidase.

Figure 2:
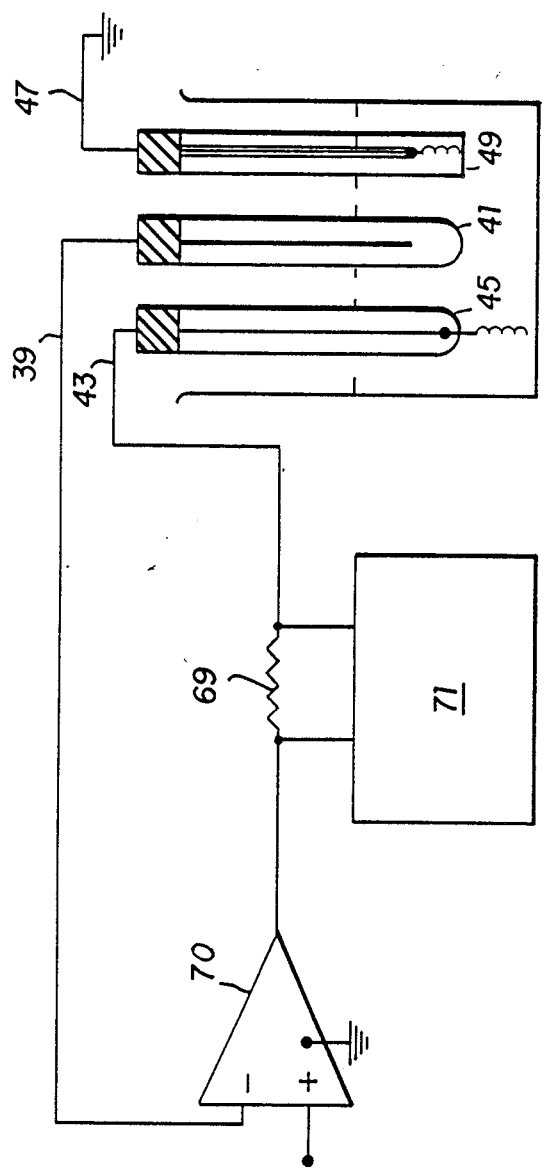
FIG. 2 is a schematic circuit diagram of an arrangement for indicating readouts of glucose concentrations in accordance with an embodiment of the invention.

Referring to FIG. 2, the leads 39, 43, and 47 for the respective electrodes—reference electrode 41, the counter electrode or cathode 45, and the working electrode or anode 49—are connected as inputs to a potentiostat amplifier 70. Such an amplifier and the connections thereto for an enzyme glucose sensor are well known in the art such as in aforementioned U.S. Pat. No. 4,703,756 and will not be described in detail. The working electrode or anode 49 puts out an electrical current having an amplitude proportional to the chemical process catalyzed by the sensor attached to it. In particular, the chemical process involved here is very well known in the art and is characterized by the decrease in oxygen and production of hydrogen peroxide resulting from the oxidation of glucose caused by reaction of the glucose with the enzyme material in inner chamber 25.

In a manner that is well known in the art, the working electrode or anode 49 provides a current having an amplitude proportional to the above-mentioned oxidation of glucose. The reference electrode 41 provides a calibrated reference voltage for the operation of the potentiostat amplifier 70. The cathode or counter electrode 45 provides a return path corresponding to the ground connection of amplifier 70. The current appearing on lead 47 is converted to a voltage proportional to such current by the amplifier 70, as is indicated by a voltage dropping resistance 70a across which may be connected a suitable monitoring or readout device such as a voltmeter 71. Of course, in a manner well known in the art, device 71 may be a voltage-controlled telemetering unit for transmitting a signal to a remote location or may be any other suitable utilization device.

Figure 3:
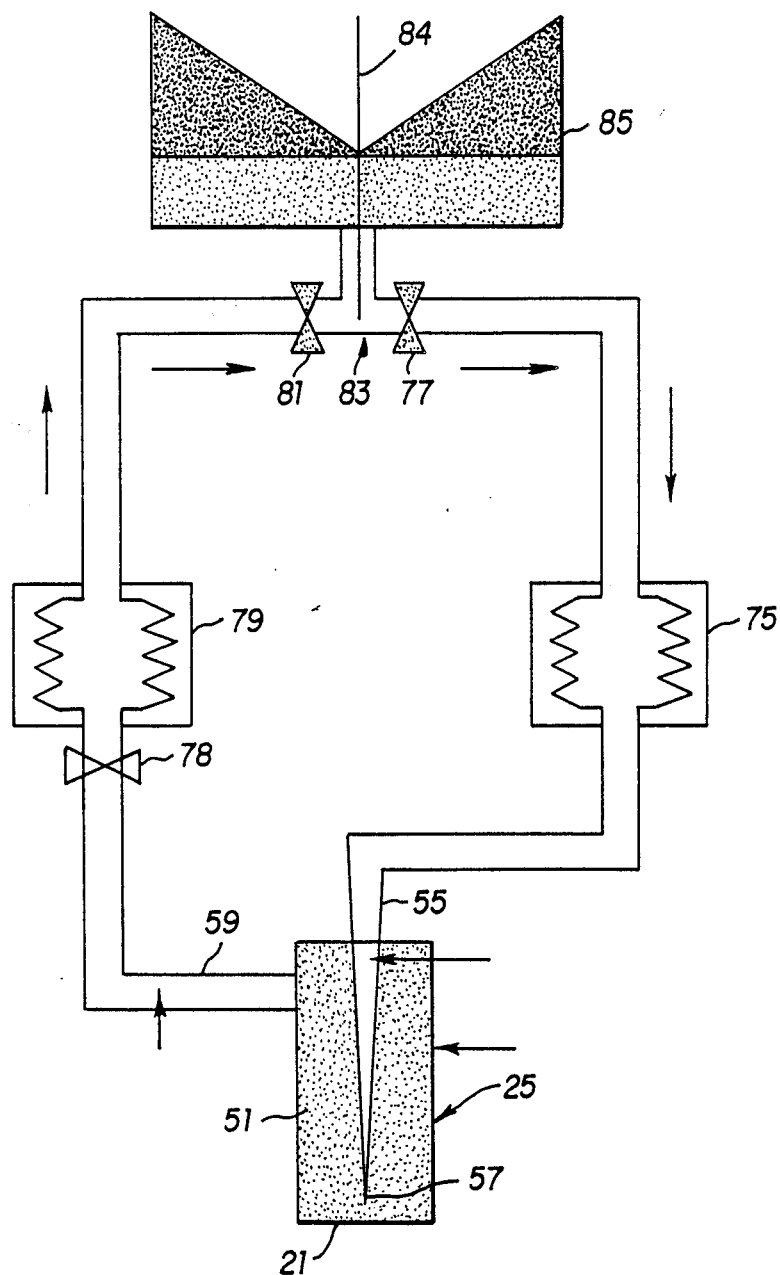
FIG. 3 is a schematic diagram of a recharging and discharging arrangement for replenishing spent enzyme material in accordance with an embodiment of the present invention.

Referring to FIG. 3, a charge tube or line 55 and discharge or exhaust tube or line 59 for respectively replenishing and exhausting the enzyme material 51 in chamber 25 are shown in a replenishment system according to an embodiment of the invention. This system may also be used for handling recharging and expelling of the catalase enzyme material 53 located in chamber 33 via tubes 63 and 69. Upstream from the feed end of the charge tube 55 is a reservoir 75 which may comprise a bellows and a one-way valve 77 of any suitable well known construction. A first valve 78 in the discharge line 59 and a reservoir 79 which also may be of the bellows type located downstream of the feed end of the discharge tube 59 for handling the spent enzyme material. A second one-way discharge valve 81 is located downstream of the reservoir 79. All of these elements may be implanted preferably near the sensor.

As further shown in FIG. 3, the charge and discharge tubes 55 and 59 converge at a junction 83 immediately adjacent valves 77 and 81 for transcutaneous reception of a needle or plurality of needles 84 via needle guide 85 of any suitable well known construction.

The procedure for charging and discharging the enzyme material will now be explained. It should be understood that the same procedure applies to handling of both the glucose oxidase in chamber 25 and the catalase in chamber 33. When the enzyme material such as the glucose oxidase is spent or degraded after use, a needle is inserted in the guide 85 to deliver fresh enzyme material to the reservoir 75. The reservoirs 75 and 79 as well as the rest of the fluid handling system including the tubes 55 and 59 are at essentially atmospheric pressure. The enzyme material, for example, glucose oxidase immobilized on fine particles of graphite suspended in the fluid described above, enters the charge reservoir 75 thereby forcing the material therein to flow through tube 55 and from opening 57 into the inner chamber 25 of sensor 10. The slight differential in pressure caused by the injection of the fresh material causes the spent material to exit chamber 25 at the feed end 35 via opening 61 of the discharge tube 59 and flow via one-way valve 78 into the discharge reservoir 79. The one-way valve 78 prevents the spent material from backing into the chamber 25.

Because the opening of tube 55 is proximate the region of the working end of the sensor near the membrane 21 and the electrode 49 in chamber 25, during replenishment the fresh enzyme material tends to be concentrated in that region where it can interact with the incoming glucose while the spent enzyme material tends to move away from that region through the opening 61 of discharge tube 59 at the feed end 35 of the sensor. When the discharge reservoir 79 becomes full, an additional needle is employed via the needle guide 85 to exhaust the spent material from the reservoir 79 at substantially the same rate the fresh material is injected into the charge reservoir 75. If desired, two needles may be used simultaneously, one for injecting fresh material and one for exhausting the spent material.

As stated previously, the recharging of the catalase material works in exactly the same way as described above for the glucose oxidase, the replenishment arrangement of FIG. 2 providing recharging of catalase via tube 63 and exhaust via tube 67 in the same manner as for respective tubes 55 and 59.

In accordance with another embodiment of the invention, the catalase enzyme material need not be employed, and thus, referring again to FIG. 1, the central housing 27 and its associated elements, the membrane 31 and the tubes 63 and 67 may be eliminated. Consequently, in accordance with this embodiment, there is provided only an outer chamber 23 and an inner chamber 25 defined by respective housings 11 and 13 and the membranes 17 and 21. Advantageously, in this embodiment the glucose oxidase enzyme material is preferably prepared as set forth in the following Example 2.:

EXAMPLE 2.

[1] Add 10 mg of glucose oxidase activity (50,000 units/0.29 g) to 42.5 mg of Bovine Serum Albumin (Sigma), and dissolve in 0.25 ml distilled water, then 0.55 ml phosphate buffer pH 7.4.;

[2] Add 0.18 ml (2.5%) Glutaraldehyde, the solution being kept in a high moisture content atmosphere for 60 minutes, and then left overnight for cross linking to take place;

[3] Provide covalent linking of the glucose oxidase on modified graphite powder in accordance with the procedure set forth in [b] above; and

[4] Add 120 mg of the immobilized glucose oxidase produced in [3] above to the cross linked enzyme produced from steps [1] and [2] above. [End of Example.]

Indications from tests employing apparatus constructed substantially in accordance with an embodiment of the invention show sustained responsiveness of the sensor to variations in glucose over a continuous four-months period. This indicates that the use of bulk amounts of immobilized and/or cross linked enzyme greatly extends the life of the sensor and thus extends the period before refill is needed.

Further, the rechargeable glucose sensor of the present invention provides these important advantages:

[i] continuous monitoring of glucose concentration;

[ii] long life time of several years afforded through recharging;

[iii] small applied voltage;

[iv] immobilization of enzymes on bulk particulate matter enabling efficient reaction with glucose and accurate measurement on a linear basis of glucose levels.

While the invention has been desribed with respect to detection and measurement of glucose levels in bodily fluids, it should be understood that the invention applies also to other compounds or molecules including, but not limited to, amino acids, lactate, or the like which exist in bodily fluids which are substrates for oxidase enzymes and require a gaseous species to undergo enzymatic conversion. Also, the invention may be applied in a laboratory environment in connection with reactor vessels or other invitro settings.

What is claimed is:

1. The method of prolonging the useful life of an electrochemical sensor implanted in a living body and of the type employing an enzyme material for reaction with components of bodily fluids and which enzyme material becomes spent or degraded after reaction comprising the steps of:

fixing the enzyme material on bulk particulate matter for reaction in the implanted sensor with a component of bodily fluids, and recharging the implanted sensor with fresh enzyme material fixed on said bulk particulate matter and removing the bulk particulate matter carrying the degraded enzyme material from the sensor.

2. The method according to claim 1 wherein the bulk particulate matter is electrically conductive particles suspended in a fluid.

3. The method according to claim 2 wherein the enzyme material is glucose oxidase and the component of bodily fluids is glucose.

4. The method according to claim 1 wherein the particulate matter comprises electrically conductive particles in bulk powder form suspended in a liquid.

5. An electrochemical sensor implantable for an extended period of time in a living body for sensing one or more components of bodily fluids comprising:

a housing having membrane means for defining reaction chamber means into which said one or more components of the bodily fluid may enter via said membrane means;

charge flow means and discharge flow means coupled to said reaction chamber means for respectively admitting to and expelling from said reaction chamber means particulate matter containing an enzyme for chemically reacting with at least one of said components, and electrode means in said reaction chamber means for producing electrical signals corresponding to the chemical reaction between the enzyme material and the component.

6. The sensor according to claim 5 wherein said reaction chamber means and membrane means comprises a first chamber having a first membrane for admitting bodily fluid into the first chamber and a second chamber having a second membrane for admitting a glucose component of said bodily fluid into the second chamber.

7. The sensor according to claim 6 wherein the enzyme consists essentially of glucose oxidase situated in said second chamber.

8. The sensor according to claim 7 wherein said reaction chamber means further comprises a third chamber containing a catalase enzyme material and said membrane means further comprises a third membrane for said third chamber separating said second chamber from the third chamber, whereby hydrogen peroxide resulting from the chemical reaction in said second chamber passes through said third membrane and is neutralized by said catalase enzyme.

9. The sensor according to claim 5 wherein said particulate matter is carried in a liquid suspension.

* * * * *

UNITED STATES PATENT AND TRADEMARK OFFICE
CERTIFICATE OF CORRECTION

PATENT NO. : 4,986,271

DATED : January 22, 1991

INVENTOR(S) : Ebtisam S. Wilkins

It is certified that error appears in the above-identified patent and that said Letters Patent is hereby corrected as shown below:

ON THE TITLE PAGE:

In the title, insert --IN-- before "VIVO".

In Col. 7, at line 19, change "invitro" to --in vitro--.

Signed and Sealed this

Twelfth Day of January, 1993

Attest:

DOUGLAS B. COMER

*Attesting Officer*  *Acting Commissioner of Patents and Trademarks*